(12) United States Patent
Shiraishi et al.

(10) Patent No.: US 10,350,681 B2
(45) Date of Patent: *Jul. 16, 2019

(54) TITANIUM ALLOY MEMBER AND PRODUCTION METHOD THEREFOR

(75) Inventors: Tohru Shiraishi, Yokohama (JP); Yoshiki Ono, Yokohama (JP); Yuji Araoka, Yokohama (JP)

(73) Assignee: NHK SPRING CO., LTD., Yokohama (JP)

( * ) Notice: Subject to any disclaimer, the term of this patent is extended or adjusted under 35 U.S.C. 154(b) by 198 days.

This patent is subject to a terminal disclaimer.

(21) Appl. No.: 14/124,058

(22) PCT Filed: Apr. 27, 2012

(86) PCT No.: PCT/JP2012/061790
§ 371 (c)(1),
(2), (4) Date: Dec. 5, 2013

(87) PCT Pub. No.: WO2012/169305
PCT Pub. Date: Dec. 13, 2012

(65) Prior Publication Data
US 2014/0212319 A1    Jul. 31, 2014

(30) Foreign Application Priority Data
Jun. 7, 2011  (JP) .................................. 2011-127233

(51) Int. Cl.
*B22F 1/00* (2006.01)
*B22F 3/10* (2006.01)
(Continued)

(52) U.S. Cl.
CPC ............ *B22F 1/0081* (2013.01); *A61L 27/06* (2013.01); *B22F 3/24* (2013.01); *C22C 1/0458* (2013.01);
(Continued)

(58) Field of Classification Search
CPC .. B22F 1/0081; B22F 1/88; B22F 3/24; C22F 1/183; C22C 1/0458; C22C 14/00; A61L 27/06
(Continued)

(56) References Cited

U.S. PATENT DOCUMENTS 5,704,239 A * 1/1998 Beals et al. ....................... 72/53
5,759,484 A   6/1998 Kashii et al.
(Continued)

FOREIGN PATENT DOCUMENTS

EP        0 555 033 A1    8/1993
JP        A-05-272526     10/1993
(Continued)

OTHER PUBLICATIONS

International Search Report issued in Application No. PCT/JP2012/061790; dated Aug. 14, 2012 (With Translation).
(Continued)

*Primary Examiner* — Keith Walker
*Assistant Examiner* — John A Hevey
(74) *Attorney, Agent, or Firm* — Oliff PLC

(57) ABSTRACT

A high strength titanium alloy member with superior fatigue resistance, and a production method therefor, are provided. The production method includes preparing a raw material made of titanium alloy, nitriding the raw material to form a nitrogen-containing raw material by generating a nitrogen compound layer and/or a nitrogen solid solution layer in a surface layer of the raw material, mixing the raw material and the nitrogen-containing raw material to yield a nitrogen-containing mixed material, sintering the nitrogen-containing mixed material to obtain a sintered titanium alloy member by bonding the material together and uniformly diffusing nitrogen in solid solution from the nitrogen-containing raw material to the entire interior portion of the sintered titanium alloy member, hot plastic forming and/or heat treating the sintered titanium alloy member to obtain a processed member, and surface treating the processed member to provide compressive residual stress.

18 Claims, 4 Drawing Sheets

(51) Int. Cl.
*B22F 3/14* (2006.01)
*B22F 3/15* (2006.01)
*B22F 3/24* (2006.01)
*C22C 1/04* (2006.01)
*C22F 1/18* (2006.01)
*C23C 8/80* (2006.01)
*A61L 27/06* (2006.01)
*B22F 3/105* (2006.01)
*C22C 14/00* (2006.01)
*C23C 26/00* (2006.01)

(52) U.S. Cl.
CPC ............. *C22C 14/00* (2013.01); *C22F 1/183* (2013.01); *C23C 8/80* (2013.01); *C23C 26/00* (2013.01); *B22F 2998/10* (2013.01)

(58) Field of Classification Search
USPC ............ 419/13, 44, 30, 32, 34, 57; 420/417, 420/418, 420, 421
See application file for complete search history.

(56) References Cited

U.S. PATENT DOCUMENTS

| | | | |
|---|---|---|---|
| 5,861,070 A * | 1/1999 | Reichman et al. | ........... 148/671 |
| 6,063,211 A | 5/2000 | Soeda et al. | |
| 7,442,266 B2 * | 10/2008 | Furuta et al. | ............ 148/421 |
| 2004/0141870 A1 | 7/2004 | Michaluk et al. | |
| 2007/0193662 A1 * | 8/2007 | Jablokov et al. | ............ 148/421 |
| 2010/0044223 A1 | 2/2010 | Tsukamoto | |
| 2010/0200123 A1 * | 8/2010 | Kirkwood et al. | ........... 148/525 |
| 2012/0168042 A1 * | 7/2012 | Lee | ........................ C22C 14/00 148/557 |
| 2014/0112819 A1 * | 4/2014 | Shiraishi et al. | ............... 419/28 |

FOREIGN PATENT DOCUMENTS

| | | |
|---|---|---|
| JP | A-08-157987 | 6/1996 |
| JP | A-2000-096208 | 4/2000 |
| JP | A-2006-022402 | 1/2006 |
| JP | A-2007-113120 | 5/2007 |
| JP | B2-4303821 | 7/2009 |
| WO | WO 96/33292 A1 | 10/1996 |
| WO | WO 2011/037127 * | 3/2011 |

OTHER PUBLICATIONS

Gil, F. Javier et al., "The effect of shot blasting and heat treatment on the fatigue behavior of titanium for dental implant applications", Dental Materials, vol. 23, No. 4, 2007, pp. 486-491.

Mar. 27, 2015 Extended Search Report issued in European Application No. 12 79 6078.9.

* cited by examiner

Photograph No.1 Sample No.4      Photograph No.2 Comparative Sample No.1

Photograph No.3 Sample No.9      Photograph No.4 Comparative Sample No.2

TITANIUM ALLOY MEMBER AND PRODUCTION METHOD THEREFOR

TECHNICAL FIELD

The present invention relates to a highly fatigue-resistant titanium alloy member used in parts that are required to be light in weight and have high strength, and relates to a production method therefor. In particular, the titanium alloy member can be suitable for parts that will be subjected to repeated stresses.

BACKGROUND ART

Titanium alloys are light in weight and have high strength and are therefore used in various fields of parts in which low weight is important, such as aircraft parts and automobile parts. Titanium alloys are also superior in corrosion resistance and biocompatibility and are also widely used in the field of biological implant devices. In any of these fields, α-β type titanium alloys, typically exemplified by Ti-6Al-4V, are common because the alloys have high strength and broad utility.

In view of these circumstances, development of increased strength in α-β type titanium alloys that have high practical utility due to low cost are actively pursued. For example, Japanese Unexamined Patent Application Laid-Open No. 5-272526 discloses a technique in which Ti-6Al-4V is subjected to gas nitriding, and a brittle TiN compound surface layer is removed, thereby improving fatigue strength. Japanese Unexamined Patent Application Laid-Open No. 2000-96208 discloses a technique in which a first layer of a nitrogen solid solution hard layer and a second layer of an oxygen solid solution hard layer are formed simultaneously on pure titanium or Ti-6Al-4V, thereby hardening a surface of the member. Japanese Patent No. 4303821 discloses a composite material in which a TiC compound is dispersed in Ti-6Al-4V.

It is well known that providing compressive residual stress to a surface of a member by shot peening or the like is effective for improving fatigue resistance of the member to be subjected to repeated stresses. Thus, research relating to shot peening to provide greater compressive residual stress is also actively pursued. For example, Japanese Unexamined Patent Application Laid-Open No. 2006-22402 discloses a technique for improving fatigue resistance. In this technique, shot peening is performed on an α-β type titanium alloy containing a β phase at 50 volume % or more or a β type titanium alloy, thereby providing not less than 270 MPa of compressive residual stress to a depth within 100 μm from the surface.

According to the techniques disclosed in Japanese Unexamined Patent Applications Laid-Open Nos. 5-272526 and 2000-96208, only the surface of the member is strengthened, and the inside of the member is difficult to strengthen. That is, the techniques are effective for improving wear resistance and preventing fatigue crack formation on the surface, but are less effective for improving static strength and preventing fatigue crack growth. In the technique disclosed in Japanese Patent No. 4303821, a titanium alloy powder and a TiC compound powder are mixed together, compacted, and then sintered. It is difficult to uniformly mix powders which have different specific gravity, and the metallic structure after the sintering is therefore not uniform. That is, low-strength portions may exist and decrease reliability of strength as a member and quality stability, and thereby the sintered compact is difficult to produce as industrial products practically.

In the technique disclosed in Japanese Unexamined Patent Application Laid-Open No. 2000-96208, the alloy contains a second layer of an oxygen solid solution hard layer in which oxygen is an α-stabilizing element as well as nitrogen. Although oxygen is an α-stabilizing element as well as nitrogen, oxygen easily forms a hard and brittle α case (α-stabilizing element rich layer) compared to nitrogen. Therefore, it is difficult to stably control the formation of the oxygen solid solution hard layer in a production process. It is generally known that the action of oxygen for high strengthening is less than that of nitrogen.

According to the technique disclosed in Japanese Unexamined Patent Application Laid-Open No. 2006-22402, compressive residual stress is not sufficiently applied in the vicinity of a surface of a member to be used under high stresses, in particular, a part to be repeatedly subjected to bending and/or torsional stresses. The α-β type titanium alloy containing the β phase at 50 volume % or more and the β type titanium alloy contain a great amount of rare metals and are more expensive than general types of α-β type titanium alloys containing β phase at less than 50 volume %. In the α-β type titanium alloy containing the β phase at 50 volume % or more and the β type titanium alloy, the static strength can be improved by age (precipitation) hardening, but the fatigue strength is not proportional to the static strength and is not sufficiently improved. This is because precipitated phase with high hardness is generated by the heat treatment and improves the static strength, but has a great difference in the hardness (or elastic strain) from the matrix primarily made of the β phase. Thus, for fatigue caused by repeated stresses, a boundary between the precipitated phase and the β phase tends to be origins of fractures. That is, it is difficult to prevent fatigue crack formation originated from the inside of the alloy only by strengthening the surface, and it is not suitable to strengthen only the surface of a member which should have fatigue resistance.

DISCLOSURE OF THE INVENTION

As described above, although development of highly strengthened titanium alloys by utilizing nitrogen has been made, there has not been provided a technique in which a member is highly strengthened in the entirety to the interior portion. There is little research regarding proof stress (or yield strength) that is an index of practical strength (that is, fatigue strength) of parts to be subjected to repeated stresses, although research is performed regarding high strength. Moreover, compressive residual stress is not sufficiently applied to the vicinity of a surface of a member, in which fatigue may be caused by high stresses, by the conventional techniques. In view of these circumstances, an object of the present invention is to provide a high strength titanium alloy member with superior fatigue resistance and a production method therefor. This titanium alloy member is made of an inexpensive α-β type titanium alloy having broad utility and has high proof stress and high strength from the surface to the entire interior portion, while at the same time having great compressive residual stress provided from the surface to the deep interior.

The present invention provides a method for producing a titanium alloy member, the method including: preparing a raw material made of titanium alloy; nitriding the raw material to form a nitrogen-containing raw material by generating a nitrogen compound layer and/or a nitrogen solid solution layer in a surface layer of the raw material; mixing the raw material and the nitrogen-containing raw material to yield a nitrogen-containing mixed material; sintering the nitrogen-containing mixed material to obtain a sintered titanium alloy member by bonding the material together and uniformly diffusing nitrogen in solid solution from the nitrogen-containing raw material to the entire interior portion of the sintered titanium alloy member; hot plastic forming and/or heat treating the sintered titanium alloy member to obtain a processed member; and surface treating the processed member to provide compressive residual stress.

According to the present invention, the sintering yields a sintered titanium alloy member in which nitrogen contained in the nitrogen-containing raw material uniformly diffuses to the entire interior portion of the sintered body by solid solution. The sintered titanium alloy member is then subjected to hot plastic forming and/or heat treating, whereby a titanium alloy member that is highly strengthened overall and that has high proof stress is obtained. When nitrogen compounds such as TiN compound are formed, difference in hardness (or elastic force) between the highly hardened TiN compound phase and the matrix is large, and the boundary thereof is easily the origin of fractures in fatigue in which repeated stress is loaded. On the other hand, in the present invention, nitrogen is contained in solid solution, and there is no boundary having a large difference in hardness and readily being an origin of fractures between the highly hardened phase such as a nitrogen compound and the matrix, whereby fatigue resistance is improved.

The material for the raw material of the present invention is preferably a widely used α-β type titanium alloy. Examples of the material may include Ti-3Al-2.5V, Ti-3Al-3Mo-1V, Ti-4Al-3Mo-1V, Ti-4Al-4Mo-2Sn, Ti-5Al-2Cr-1Fe, Ti-5Al-1.5Fe-1.5Cr-1.5Mo, Ti-5Al-2Sn-2Zr-4Mo-4Cr, Ti-6Al-2Sn-2Zr-2Mo-2Cr, Ti-6Al-2Sn-4Zr-6Mo, Ti-6Al-2Sn-4Zr-2Mo, Ti-5Al-6Sn-2Zr-1Mo, Ti-6Al-2Cb-1Ta-1Mo, Ti-6Al-4V, Ti-6Al-6V-2Sn, Ti-7Al-4V, Ti-8Al-1Mo-1V, Ti-8Al-4Co, Ti-8Mn, and Ti-25Al-11Sn-5Zr-1Mo.

Powders, thin strips, thin pieces, and fibers may be used for the raw material. Among these forms, thin strips, thin pieces, and fibers are preferable in view of handling and safety. These forms can easily be the same size, whereby control of amount of nitrogen in the nitriding, that is, control of amount of nitrogen contained in a sintered titanium alloy member can be easy, and therefore, thin strips, thin pieces, and fibers are preferable to powders. Fibers that are obtained by production methods for woven cloth and unwoven cloth are more preferable to thin strips and thin pieces. The production methods for woven cloth and unwoven cloth enable a more uniform mixing of a raw material and a nitrogen-containing raw material, whereby nitrogen can easily diffuse more uniformly to a sintered titanium alloy member overall. As for the method of producing fibers, a molten metal extraction method is most suitable because titanium alloy fibers having superior cleanliness can be produced. Thus, the raw material is preferably formed of titanium alloy fibers produced by the molten metal extraction method.

The sintering may be preferably performed by hot pressing, hot isostatic pressing, or spark plasma pressure sintering, which have a compressing mechanism and enable sintering in a vacuum or in an inert gas atmosphere. By heating to a predetermined temperature and compressing the nitrogen-containing mixed material, a sintered titanium alloy member containing few pores and nitrogen that is uniformly diffused can be obtained.

Then, by hot plastic forming the sintered titanium alloy member, pores, which negatively affect the fatigue resistance as defects, can be decreased to zero or nearly zero. Thus, a processed member containing no pores or almost no pores and uniformly diffused nitrogen is obtained.

The hot plastic forming may be performed by forging, rolling, drawing, or extruding. The forging is preferably performed to form a member into a near net shape. The rolling is preferably performed to form a thin sheet member which will be formed into the shape of a product by subsequent press forming. By the drawing or the extruding, the sintered titanium alloy member is deformed and is provided with larger internal strain, whereby a more densified processed member having high strength and high proof stress can be obtained. The densified processed member does not or barely contains pores that can become origins of fractures in fatigue in which repeated stress is loaded, whereby high fatigue resistance is stably obtained.

By hot plastic forming the sintered titanium alloy member, a finely deformed structure made of an α-β phase is obtained. The finely deformed structure is work hardened by strain accumulation, and it has a great number of grain boundaries that are perpendicular or curved with respect to directions of crack growth, and thereby has a great effect for preventing crack growth by stopping and curving cracks. Accordingly, fatigue resistance is further improved. Thus, the titanium alloy member obtained after the hot plastic forming is preferably formed of the finely deformed structure for improving the fatigue resistance.

In particular, the finely deformed structure preferably has not less than 30% of "$GOS_{\geq 3°}$", The GOS (Grain Orientation Spread) is calculated as the average misorientation among all pixels in a grain. The "$GOS_{\geq 3°}$" represents an area ratio of grains with not less than 3° of GOS to the entire observation visual field. When the "$GOS_{\geq 3°}$" is less than 30%, the structure is not sufficiently deformed, and thereby the above effects are not sufficiently obtained, and fatigue resistance decreases. Moreover, since pores tend to be origins of fractures in fatigue, which occurs when repeated stress is loaded, the porosity is preferably less than 0.65 pores/mm$^2$ so as to reliably obtain high fatigue resistance. The porosity is the number of pores per area (porosity (pores/mm$^2$)=total number of pores/(visual field area×30)), which is determined by counting observable pores at freely selected 30 areas when a cross sectional structure of a titanium alloy member is observed at a 100-times magnification (visual field area of 1.1 mm$^2$) using an electron microscope.

The heat treating is performed on the sintered titanium alloy member by solution heat treatment and then annealing treatment, whereby a processed member having a uniform fine acicular structure that is thermally stable is obtained. By forming a uniform fine acicular structure which is thermally stable, the amount of nitrogen can be increased whereas embrittlement is inhibited, and further high strength and high fatigue strength are achieved. Forming such a fine acicular structure in the heat treating is effective for improving the fatigue strength because fine grains increase strength and the acicular structure is highly resistant to crack progression.

The solution heat treatment in the present invention is performed by heating a material to a temperature near the β transus temperature and then rapidly cooling in a cooling medium. The heating temperature for an α-β type titanium alloy is preferably within ±100° C. from the β transus temperature. By this treatment, a fine acicular structure primarily made of α' phase (hexagonal martensite) is obtained. If the heating temperature exceeds 100° C. from the β transus temperature, the β phase may coarsen by heating, thereby precipitating coarse α phase at grain boundaries after cooling. As a result, ductility of the member is greatly reduced. If the heating temperature is lower than 100° C. from the β transus temperature, transformation of an α phase into a β phase in heating is insufficient, and therefore a large amount of coarse α phase remains, and required strength is difficult to obtain.

The annealing treatment after the solution heat treatment is performed by suitably recovering and resolving supersaturated solid solutions such as an α' phase which is hard, brittle, and thermally unstable, thereby thermally stabilizing the structure and improving mechanical properties by fine precipitated phases. The heating temperature for an α-β type titanium alloy is preferably 450 to 750° C. By this treatment, a fine α phase precipitates in the residual β phase and the α' phase resolves into fine α phase and β phase, whereby the member thermally stabilizes and toughness is improved. If the heating temperature is less than 450° C., the structure does not easily resolve. If the heating temperature is more than 750° C., the structure thermally stabilizes, but the grains coarsen. It should be noted that the structure after the solution heat treatment is not thermally stable, but the structure is fine and strengthened by nitrogen solid solution, whereby the strength is sufficiently high compared to members before the solution heat treatment and aging (precipitating) hardened β type titanium alloy members. Thus, if thermal stability is negligible in practical use, the annealing treatment can be omitted.

The hot plastic forming and/or the heat treating are performed depending on necessary mechanical characteristics of a titanium alloy member. The hot plastic forming provides high proof stress, high ductility, and high toughness, whereby a titanium alloy member with superior fatigue resistance is obtained. The heat treating provides high hardness, although providing slightly less fatigue resistance due to lower ductility and toughness compared with the hot plastic forming, whereby a titanium alloy member with superior wear resistance and fatigue wear resistance is obtained. The hot plastic forming is performed prior to the heat treating when both steps are necessary.

The processed member is then subjected to the surface treating to provide compressive residual stress, whereby a high fatigue resistant titanium alloy member having great compressive residual stress from the surface to a deep interior is obtained. The surface treating is preferably performed by shot peening, but various means for providing compressive residual stress to the vicinity of the surface, such as ultrasonic peening or cavitation peening, can be appropriately selected according to its effects.

The compressive residual stress provided by the surface treating is preferably 880 MPa or higher at the maximum. Moreover, an integrated value $I_{-oR}$ of compressive residual stress from the surface to a crossing point is preferably 100 MPa·mm or higher. The crossing point is a depth from the surface of the titanium alloy member, where the compressive residual stress provided to the vicinity of the surface, is zero. By thus providing compressive residual stress, a titanium alloy member with superior fatigue resistance is obtained.

The proof stress (or yield stress) closely relates to the degree of the compressive residual stress introduced by the surface treating, and great compressive residual stress is more easily obtained from the surface to a deep interior when the proof stress (or yield stress) is greater. In the present invention, 0.2% bending proof stress of the titanium alloy member is preferably 1600 MPa or higher so as to obtain the above-described degree of compressive residual stress.

In the present invention, the titanium alloy member preferably contains 0.02 to 0.13 mass % of nitrogen in solid solution. By uniformly diffusing nitrogen in solid solution, the titanium alloy member is strengthened overall and has high proof stress, whereby the fatigue resistance is improved. These effects are not sufficiently obtained when the amount of nitrogen is less than 0.02%, whereas the ductility greatly decreases and the titanium alloy member becomes brittle when the amount of nitrogen is greater than 0.13%.

The present invention also provides a titanium alloy member that can be obtained by the above-described production method, and the titanium alloy member contains nitrogen at 0.02 to 0.13 mass % in solid solution and has a surface provided with compressive residual stress. Since not less than 0.02% of nitrogen uniformly diffuses by solid solution, the titanium alloy member of the present invention is strengthened overall and has high proof stress, whereby the fatigue resistance is improved.

The titanium alloy member of the present invention can be used for parts which must be reduced in weight, such as aircraft parts and automobile parts, and in particular, the titanium alloy member is suitably used for parts that should have high strength. The titanium alloy is superior in corrosion resistance and in biocompatibility, and therefore, the titanium alloy member is preferably used for biological implant devices. In particular, the titanium alloy member is more preferably used for biological implant devices that should have high strength because the benefit of its low weight is obtained to a high degree.

Effects of the Invention

According to the present invention, a high strength titanium alloy member with superior fatigue resistance is obtained. The titanium alloy member is made of an inexpensive α-β type titanium alloy having broad utility and has high proof stress and high strength from the surface to the entire interior portion, while having great compressive residual stress provided from the surface to the deep interior.

BRIEF DESCRIPTION OF THE DRAWINGS

FIG. 1A is a schematic side sectional view of the overall apparatus, and FIG. 1B is a sectional view of a circumferential edge of a disk used in the apparatus.

FIG. 2A is a side view of the fiberizing apparatus and FIG. 2B is a partially enlarged view of the fiberizing apparatus.

Figure 1A:
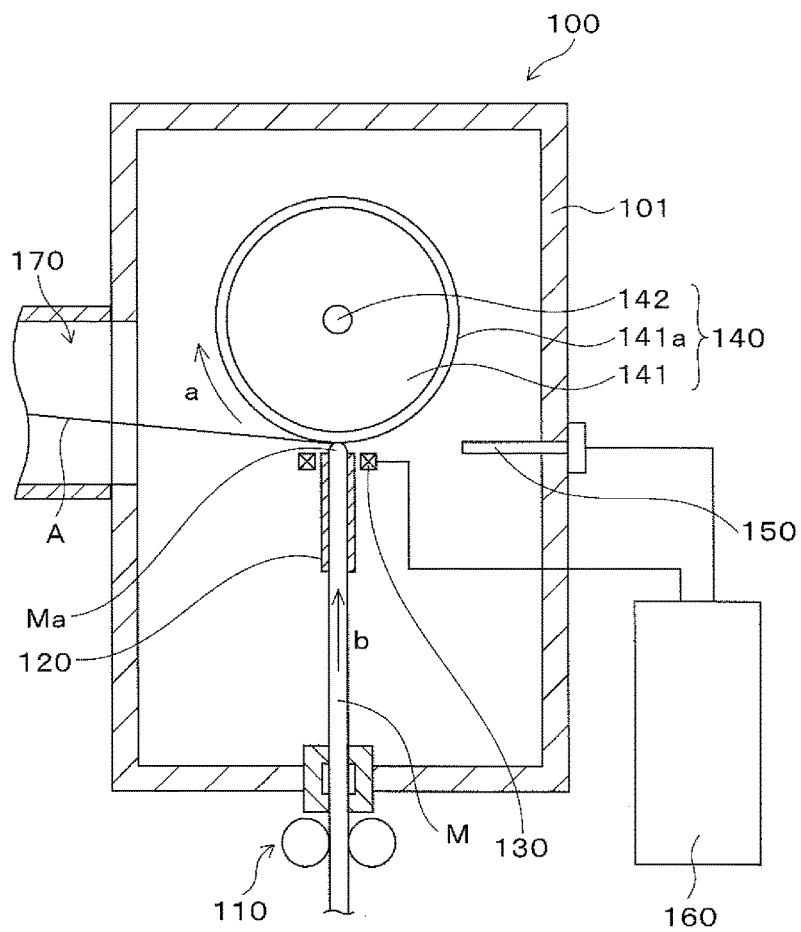
FIGS. 1A and 1B show a metal fiber producing apparatus used in an embodiment of the present invention.

EXPLANATION OF REFERENCE NUMERALS 100 denotes a metal fiber producing apparatus, 101 denotes a chamber, 110 denotes a material feeding portion, 120 denotes a material holding portion, 130 denotes a heating portion, 140 denotes a disk rotating portion, 141 denotes a disk, 141a denotes a circumferential edge, 142 denotes a rotating shaft, 150 denotes a temperature measuring portion, 160 denotes a high-frequency generating portion, 170 denotes a metal fiber receiving portion, 200 denotes a fiberizing apparatus, 210 denotes a material conveyer, 211 denotes a feed roller, 212 denotes a fiberizing mechanism, 213 denotes a conveyer, 214 denotes a belt, 300 denotes an extruding apparatus, 305 denotes an outer die, 310 denotes a container, 320 denotes a lower die, 330 denotes a die, 340 denotes a punch, 360 denotes a heater, A denotes a raw material, B denotes a nitrogen-containing raw material, A+B denotes a nitrogen-containing mixed material, C denotes a sintered titanium alloy member, M denotes a material, and Ma denotes a molten material.

Embodiment of the Invention

A method for producing the titanium alloy member of the present invention will be specifically described. It should be noted that the apparatuses used in the following method are merely an embodiment, and other apparatuses may also be used.

(1) Preparing Step

Figure 1B:
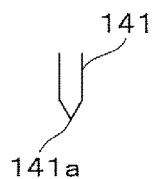

FIGS. 1A and 1B schematically show a metal fiber producing apparatus 100 for obtaining a raw material A (hereinafter called an "apparatus 100"). FIG. 1A is a schematic side sectional view of the overall apparatus 100, and FIG. 1B is a sectional view of a circumferential edge 141a of a disk 141 used in the apparatus 100. FIG. 1B is a side sectional view in a direction perpendicular to the plane of the paper.

The apparatus 100 is a metal fiber producing apparatus using a molten metal extraction method. In the apparatus 100, an upper end portion of a rod-shaped material M melts, and the molten material Ma contacts the circumferential edge 141a of the rotating disk 141. Then, a portion of the molten material Ma is extracted toward an approximately tangential direction of the circumference of the disk 141 and is rapidly cooled, and thereby a titanium alloy fiber is formed as a raw material A. For example, an α-β type titanium alloy such as Ti-6Al-4V is used as a material M for a raw material A, and a raw material A having a diameter of 10 to 200 μm is produced. The diameter of the raw material A is not particularly limited and is appropriately selected according to the amount of nitrogen that should be contained in the titanium alloy member. For example, when a larger amount of nitrogen should be contained, the diameter of the raw material A may be thinner. In this case, the proportion of a nitrogen compound layer and/or a nitrogen solid solution layer which are formed by the nitriding can be increased with respect to the diameter.

As shown in FIG. 1A, the apparatus 100 includes a sealable chamber 101 containing a material feeding portion 110, a material holding portion 120, a heating portion 130, a disk rotating portion 140, a temperature measuring portion 150, a high-frequency generating portion 160, and a metal fiber receiving portion 170.

The chamber 101 is evacuated or is filled with an inert gas as an atmosphere so as to inhibit reaction of impurities such as oxygen and the molten material Ma. For example, an argon gas can be used for the inert gas atmosphere. The material feeding portion 110 is located, for example, at the bottom of the chamber 101, feeds the material M toward the direction of the arrow "b" at a predetermined speed, and provides the material M to the material holding portion 120. The material holding portion 120 prevents movement of the molten material Ma toward a radial direction thereof and guides the material M to a suitable position of the disk rotating portion 140.

The material holding portion 120 is a water-cooled metal tubular member and is located below the disk 141 between the material feeding portion 110 and the metal fiber forming portion 140. The heating portion 130 is a high-frequency induction coil that generates magnetic flux for melting the upper end portion of the material M and forming the molten material Ma. As a material for the material holding portion 120, a material that has high thermal conductivity for cooling effect by a cooling water and is non-magnetic to avoid effects of the magnetic flux generated by the heating portion 130 is preferable. Copper or copper alloy is preferable as a material for the material holding portion 120 for practical use.

The disk rotating portion 140 produces a raw material A from the molten material Ma by the disk 141 which rotates around a rotating shaft 142. The disk 141 is made from, for example, copper or copper alloy having high thermal conductivity. As shown in FIG. 1B, a V-shaped circumferential edge 141a is formed on the circumferential portion of the disk 141.

The temperature measuring portion 150 measures the temperature of the molten material Ma. The high-frequency generating portion 160 supplies high-frequency current to the heating portion 130. The power of the high-frequency generating portion 160 is controlled based on the temperature of the molten material Ma, which is measured by the temperature measuring portion 150, and thereby the temperature of the molten material Ma is maintained constant. The metal fiber receiving portion 170 receives the raw material A which is formed by the metal fiber forming portion 140.

In the apparatus 100 constructed in this way, first, the material feeding portion 110 continually feeds the material M in the direction of the arrow "b", thereby supplying it to the material holding portion 120. The heating portion 130 melts the upper end portion of the material M by induction heating, thereby forming the molten material Ma. Then, the molten material Ma is continually fed to contact the circumferential edge 141a of the disk 141 rotating in the direction of the arrow "a", and a part thereof is extracted toward an approximately tangential direction of the circumference of the disk 141 and is rapidly cooled, whereby a raw material A is formed. The formed raw material A extends toward the approximately tangential direction of the circumference of the disk 141 and is received by the metal fiber receiving portion 170 which is located in the direction in which the raw material A extends.

(2) Nitriding Step

In the nitriding step, an aggregate of the raw material A produced in the preparing step is carried into a vacuum furnace, which is then evacuated and supplied with a nitrogen gas, and the raw material A is heated. In this case, an inert gas such as an argon gas may be supplied with the nitrogen gas for adjusting the density and the pressure of the nitrogen gas. The pressure and the temperature in the furnace and processing time are suitably selected according to amount of nitrogen which should be contained in a titanium alloy member.

If the temperature in the furnace is too low, a very long time is required to form a nitrogen compound layer and/or a nitrogen solid solution layer. If the temperature in the furnace is too high, the processing time is difficult to control because the reaction rate is high, and a thick nitrogen compound layer is readily formed. The thick nitrogen compound layer requires a very long time for diffusing nitrogen in a subsequent sintering step. Thus, the temperature in the furnace is preferably 600 to 1000° C. for practical production. By the nitriding step, a nitrogen-containing raw material B in which a very thin TiN compound layer and/or nitrogen solid solution layer is formed in a surface layer of the raw material A is produced.

(3) Mixing Step

Figure 2A:
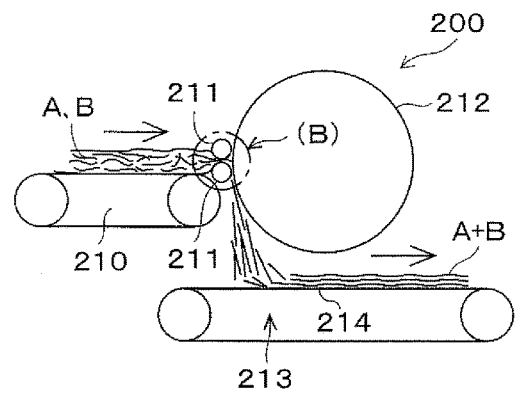
FIGS. 2A and 2B show a fiberizing apparatus used in an embodiment of the present invention.

The raw material A and the nitrogen-containing raw material B are mixed together with predetermined percentage according to amount of nitrogen which should be contained in a titanium alloy member. As a mixing means, for example, a fiberizing apparatus 200 shown in FIG. 2A is used. Appropriate amounts of an aggregation of the raw material A and an aggregation of the nitrogen-containing raw material B are supplied to a material conveyer 210 and are moved to the exit side. A feed roller 211 is located at the exit of the material conveyer 210. A fiberizing mechanism 212 is located outside of the feed roller 211.

Figure 2B:
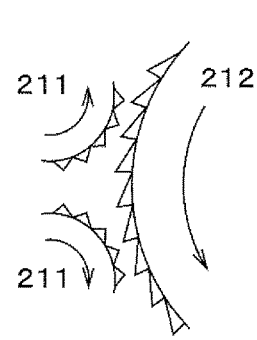

As shown FIG. 2B, the feed roller 211 includes numerous feeding teeth provided on the circumference thereof, and the feeding teeth bite and feed the raw material A and the nitrogen-containing raw material B. The fiberizing mechanism 212 includes numerous fiberizing teeth provided on the circumference thereof, and the fiberizing teeth comb a part of the raw material A and the nitrogen-containing raw material B, which are fed from the feed roller 211, and drop it on a belt 214 of a conveyer 213. In this condition, the raw material A and the nitrogen-containing raw material B are cut and mixed and are piled up on the belt 214 as an aggregation of random fibers without orientation in a cross section in a direction approximately perpendicular to the belt 214, whereby a nitrogen-containing mixed material A+B is formed. As a mixing means other than the fiberizing apparatus 200 shown in FIG. 2A, various means can be appropriately used. For example, unwoven fabric forming machines, such as of the card type and the aeration type, and mixing machines such as mixers and mills can be used.

(4) Sintering Step

The nitrogen-containing mixed material A+B is sintered by an apparatus that has a pressurizing mechanism and that can be evacuated or be purged with an inert gas. In the case of a vacuum HP (Hot Press) apparatus, a heating chamber is arranged in a vacuum vessel, and a mold is arranged within the heating chamber. In this case, a cylinder is provided at the upper side of the vacuum vessel, a press ram projected from the cylinder is vertically movable in the heating chamber, and an upper punch installed at the press ram is inserted into the mold. The nitrogen-containing mixed material A+B is charged into the mold of the vacuum HP apparatus as constructed above, the vacuum vessel is evacuated or purged with an inert gas, and the heating chamber is heated to a predetermined sintering temperature. Then, the nitrogen-containing mixed material A+B is compressed by the upper punch inserted into the mold, and is sintered.

The sintering should be performed in a vacuum or an inert atmosphere to avoid contamination by impurities such as oxygen from the atmosphere into a titanium alloy member.

The sintering temperature is preferably 900° C. or more, the sintering time is preferably 30 minutes or more, and the pressure of pressing is preferably 10 MPa or more. By sintering the nitrogen-containing mixed material A+B in such conditions, a sintered titanium alloy member C containing few pores can be obtained. Nitrogen contained in the nitrogen-containing raw material B uniformly diffuses into the entire interior portion of the sintered titanium alloy member C by solid solution during the sintering. Thus, the formed sintered titanium alloy member C contains no nitrogen compounds or contains very few nitrogen compounds, and has a plate-like structure composed of an $\alpha$-$\beta$ phase.

(5-1) Hot Plastic Forming Step

Figure 3:
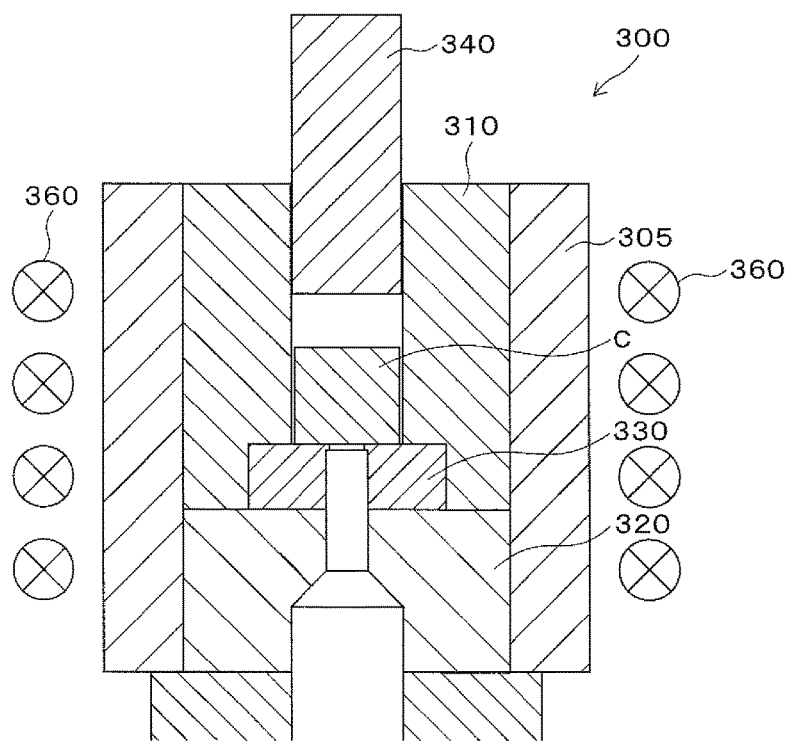
FIG. 3 is a side sectional view of an extruding apparatus used in an embodiment of the present invention.

The sintered titanium alloy member C can be subjected to hot plastic forming. The hot plastic forming is performed by, for example, an extruding apparatus shown in FIG. 3. The extruding apparatus 300 has an outer die 305 containing a tubular container 310, and a lower die 320 is coaxially arranged at an end side of the container 310. A die 330 is arranged between the container 310 and the lower die 320, and a punch 340 can be slidably inserted into the container 310. A heater 360 is arranged around the container 310.

The sintered titanium alloy member C is preliminarily heated by an outer furnace. After the sintered titanium alloy member C is charged into the container 310, the punch 340 moves down and compresses the sintered titanium alloy member C. The compressed sintered titanium alloy member C is extruded to the space inside the lower die 320 while being reduced in diameter by the die 330, whereby an extruded material is formed. The heating temperature of the sintered titanium alloy member C in the outer furnace may be 800 to 1200° C., the extrusion ratio may be 2 to 7, and the forward speed of the punch 340 may be 1 to 30 mm/second. By extruding the sintered titanium alloy member C in such conditions, all or almost all pores remaining after the sintering are removed, and a high strength and high proof stress processed member having a fine deformed structure composed of an $\alpha$-$\beta$ phase can be obtained.

The conditions such as the heating temperature and the extrusion ratio in the extruding have a complicated relationship with each other in conjunction with the material composition of the titanium alloy and the effects of the contained nitrogen, and they are suitably determined by theory, experience, and experiment. Although the fine deformed structure is obtained by setting the heating temperature and the extrusion ratio in this embodiment, an appropriate heating temperature and appropriate processing parameters should be set to obtain the fine deformed structure according to the processing method when a processing method other than the extruding is used.

(5-2) Heating Step

The solid solution treatment and the annealing treatment in the heating step can be performed in the air in a general type of heating furnace. In the solution heat treatment, the material is preferably rapidly cooled by a cooling medium such as water or oil after heating. In the annealing treatment, cooling conditions after heating are not specifically limited, and natural cooling or air stream cooling is typically performed. By heating the sintered titanium alloy member (or sintered titanium alloy member after the hot plastic forming) C at a temperature in the range within ±100° C. of the $\beta$ transus temperature, a processed member having a fine acicular structure primarily made of $\alpha'$ phase (hexagonal martensite) can be obtained. The annealing treatment may be performed at a heating temperature of 450 to 750° C. Thus, a fine $\alpha$ phase precipitates in the residual $\beta$ phase and the $\alpha'$ phase resolves into fine α phase and β phase, whereby the member thermally stabilizes and toughness is improved.

(6) Surface Treating Step

The processed member is then subjected to a surface strengthening treatment, such as shot peening, after the hot plastic forming step and/or the heating step, whereby the titanium alloy member of the present invention is obtained. The shot peening can be performed by a general method. In the case of multistep shot peening, for example, an air blast shot peening apparatus is used, and a first shot peening is performed by using a shot with a grain diameter of 0.2 to 1.2 mm and hardness of 200 to 900 HV at an air pressure of 0.1 to 0.9 MPa so that the coverage is 100% or more. Then, a second shot peening may be performed by using a $SiO_2$ powder with an average grain diameter of 0.02 to 0.15 mm as shot at an air pressure of 0.1 to 0.6 MPa so that the coverage is 100% or more.

EXAMPLES

The present invention will be described in detail by way of specific examples.

1. Production of Samples (1) Preparation of Raw Material (Preparing Step)

A raw material with an average wire diameter of 60 μm was produced from Ti-6Al-4V (corresponding to ASTM B348 Gr. 5) using the apparatus 100 shown in FIG. 1A.

(2) Preparation of Nitrogen-Containing Raw Material (Nitriding Step)

A part of the raw material was subjected to nitriding as follows. First, the raw material was carried into a vacuum furnace. After evacuating, a nitrogen gas was fed into the vacuum furnace, and the pressure in the furnace was set at 80 kPa. Then, the temperature in the furnace was increased to 800° C. and maintained for 1.5 hours.

(3) Preparation of Nitrogen-Containing Mixed Material (Mixing Step)

The raw material and the nitrogen-containing raw material were supplied to the fiberizing apparatus 200 shown in FIGS. 2A and 2B and mixed together, whereby a nitrogen-containing mixed material was obtained. The weight percentage (Wf) of the mixed nitrogen-containing raw material is shown in Table 1.

(4) Preparation of Sintered Titanium Alloy Member (Sintering Step)

The nitrogen-containing mixed material was charged into a carbon mold, and a sintered titanium alloy member having a thickness of 28 mm was obtained by a vacuum HP apparatus. After the vacuum chamber was evacuated to the degree of vacuum of $1×10^{-2}$ Pa or less and purged with an argon gas so as to be at 80 kPa, the sintering was performed at a temperature increasing rate of 10° C./minute, a sintering temperature of 1100° C., and a pressure of press of 40 MPa for 1.5 hours, and cooling was then performed in the furnace. The carbon mold and the nitrogen-containing mixed material as well as the sintered titanium alloy member which is a sintered body of the mixed material are reactive under the high temperature conditions described above. In view of this, a release plate as a liner made from $Al_2O_3$ (alumina, purity of 99.5% or more) was preliminarily installed to the carbon mold.

(5-1) Preparation of Processed Member (Hot Plastic Forming Step)

The sintered titanium alloy member was formed into a shape with a diameter of 25 mm and a height of 90 mm by machining and was heated in an outer furnace. Then, the sintered titanium alloy member was hot plastic formed by the extruding apparatus 300 shown in FIG. 3, whereby a processed member was prepared (Samples Nos. 1 to 8). The heating temperature in the outer furnace was 1100° C., the temperature of the container was 300° C., the forward speed of the punch was 10 mm/second, and the extrusion ratio was 4. The sintered titanium alloy member was preliminary applied with an antioxidizing lubricating agent (Delta-Glaze349 manufactured by Acheson Japan) before heating. The time from taking out the sintered titanium alloy member from the outer furnace to starting to advance the punch was approximately 30 seconds. The extruded titanium alloy member was water cooled right under the lower die.

(5-2) Preparation of Processed Member (Heating Step)

The sintered titanium alloy member other than that subjected to the hot plastic forming was subjected to the solid solution treatment and the subsequent annealing treatment, whereby another processed member (Sample No. 9) was prepared. In the solid solution treatment, the sintered titanium alloy member was maintained at 1040° C. for 2 hours and was then cooled in ice water. In the annealing treatment, the sintered titanium alloy member was maintained at 550° C. for 2 hours and then air-cooled. These treatments under these conditions are described as a "heat treatment" hereinafter, unless otherwise stated.

(6) Preparation of Titanium Alloy Member (Surface Treating Step)

The processed member (Samples Nos. 1 to 9) was subjected to multistep shot peening, whereby a titanium alloy member was prepared. A first shot peening was performed at an air pressure of 0.4 MPa (Samples Nos. 1 to 8) or 0.5 MPa (Sample No. 9) and at an injection distance of 50 mm by an air blast shot peening apparatus using shot with 0.80 RCW (600 HV, manufactured by Toyo Seiko Co., Ltd.) so that the coverage was 200%. Then, a second shot peening was performed at an air pressure of 0.5 MPa and at an injection distance of 50 mm by the air blast shot peening apparatus using a $SiO_2$ powder with an average grain diameter of 0.05 mm as shot so that the coverage was 200%.

(7) Preparation of Comparative Sample

For comparison, a rod of an expanded material of Ti-6Al-4V (corresponding to ASTM B348 Gr. 5) was prepared and was subjected to the hot plastic forming and the surface treating with the same conditions as described above, whereby a comparative sample No. 1 was prepared. In addition, the expanded material was subjected to the heat treatment with the same condition as described above, whereby a comparative sample No. 2 was prepared.

TABLE 1

| Sample | Wf (%) | Hot plastic forming | Heat treatment |
|---|---|---|---|
| No. 1 | 5 | Done | Not done |
| No. 2 | 10 | Done | Not done |
| No. 3 | 15 | Done | Not done |
| No. 4 | 20 | Done | Not done |
| No. 5 | 25 | Done | Not done |
| No. 6 | 30 | Done | Not done |
| No. 7 | 35 | Done | Not done |
| No. 8 | 40 | Done | Not done |
| No. 9 | 20 | Not done | Done |
| Comparative sample No. 1 | — | Done | Not done |
| Comparative sample No. 2 | — | Not done | Done |

2. Evaluation Items and Evaluation Methods

Evaluation items and evaluation methods will be described hereinafter. The evaluation results are shown in Table 2.

(1) Structure

Figure 4:
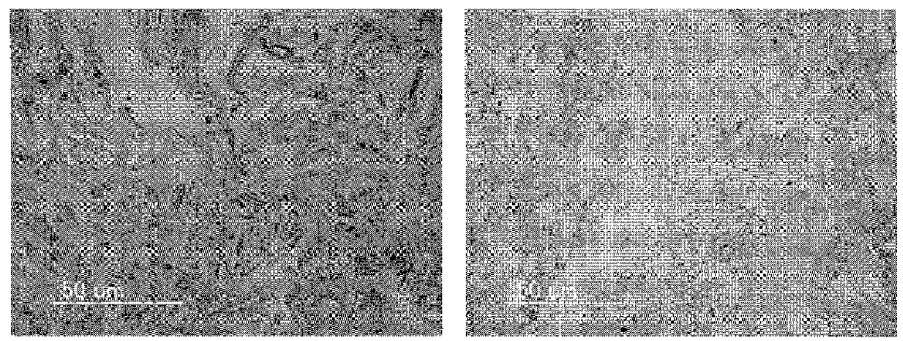
FIG. 4 shows photographs of structures of titanium alloy members in the Example.
Figure 4:
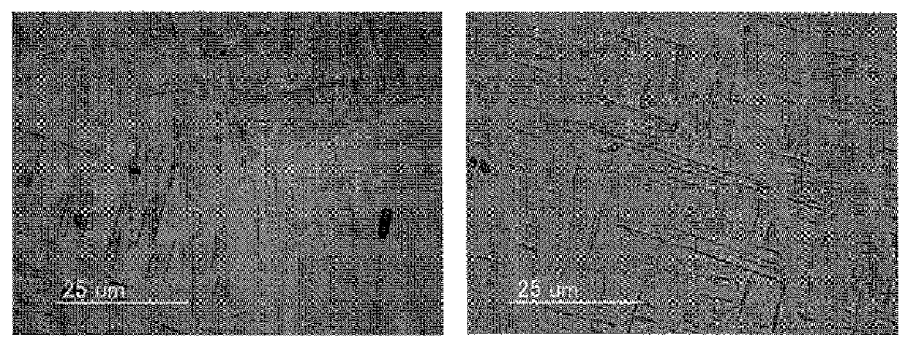

Each sample was cut into a suitable size and embedded in a resin so that the cross sectional structure perpendicular to the axial direction could be observed. Then, the embedded sample was mirror finished by mechanical polishing and was etched by an etching fluid (2 wt % of hydrofluoric acid and 4 wt % of nitric acid), and the structure was observed by an optical microscope (NIKON ME600). FIG. 4 shows typical microscope photographs of the samples. A fine deformed structure composed of an α-β phase is represented by the symbol "A" and a fine acicular structure composed of an α-β phase is represented by the symbol "B" in Table 2.

(2) Existence of TiN Compound Phase (TiN Phase)

The crystal structure was analyzed by an X-ray diffractometer (Rigaku X-ray Diffractometer RINT2000) using Cu tube target, and peak of TiN compound phase was observed.

(3) Amount of Nitrogen (N Amount)

Amount of nitrogen was measured by inert gas melting-thermal conductivity technique and solid state type infrared absorption method (LECO TC600).

(4) Area Ratio of Grains with not Less than 3° of Average Misorientation in Grain $(GOS_{\geq 3°})$ A GOS (Grain Orientation Spread: An average misorientation among all pixels in a grain) map was formed by FE-SEM/EBSD (Electron Back Scatter Diffraction) method (JEOL JSM-7000F, TSL solutions OIM-Analysis Ver. 4.6) at 1000-times magnification. Then, an area ratio of grains with not less than 3° of GOS to the entire observation visual field $(GOS_{\geq 3°})$ was calculated.

(5) Hardness (HV)

Hardness of the vicinity of the surface and the center of each sample in a cross section perpendicular to the axial direction were measured by a Vickers hardness tester (FUTURE-TECH FM-600). The test load was 10 gf. The hardness of the vicinity of the surface was measured at 10 points at 1 mm below the outer circumferential surface and the center hardness was measured at 10 points at the center and the vicinity of the center of the cross section, and the averages were calculated.

(6) Surface Roughness (Ra, Rz)

An arithmetic average roughness (Ra) and a maximum height (Rz) were measured by a non-contact three-dimensional shape measuring apparatus (MITAKA NH-3) according to the method specified in JIS B0601. The measurement magnification was 100, the measurement distance was 4 mm, and the measurement pitch was 0.002 mm. The values of Ra and Rz were calculated by setting the cut-off value at 0.8 mm.

(7) Maximum Compressive Residual Stress Value $(-\sigma_{Rmax})$, Crossing Point (CP), Integrated Value of Compressive Residual Stress $(I_{-\sigma R})$ Residual stress in the axial direction of the sample was measured by an X-ray diffraction method (Bruker AXS D8 Discover) according to the 2D method. In this case, a Cu tube target was used, the diameter of the collimator was 0.8 mm, and the Ti (213) diffraction line was used. The residual stress distribution in a depth direction from the surface toward the inside of the sample was determined by repeating chemical polishing of the entire surface and measuring. Then, a maximum compressive residual stress value $(-\sigma_{Rmax})$ in the residual stress distribution in the depth direction was determined, and the depth at which the residual stress was zero was determined as a crossing point (CP). Moreover, an integrated value $(I_{-\sigma R})$ of the residual stress from the surface to the CP was calculated.

(8) Bending Strength $(\sigma_b)$, 0.2% Bending Proof Stress $(\sigma_{b0.2})$

A three-point bending test was performed by a 300 kN universal testing machine (INSTRON 5586 type). The test piece had a width of 6 mm, a length of 17 mm, and a thickness of 1 mm, and the distance between fulcrums was 15 mm. An average of bending strength (maximum bending stress) and an average of 0.2% bending proof stress were calculated by testing three pieces of each sample at a rate of 6 mm/minute.

TABLE 2

| Sample | Structure | TiN phase | N amount (mass %) | $GOS_{\geq 3°}$ (%) | HV Surface | HV Center | Surface roughness (μm) Ra | Surface roughness (μm) Rz | $-\sigma_{Rmax}$ (MPA) | CP (mm) | $I_{-\sigma R}$ (MPa · mm) | $\sigma_b$ (MPa) | $\sigma_{b0.2}$ (MPa) |
|---|---|---|---|---|---|---|---|---|---|---|---|---|---|
| No. 1 | A | Not recognized | 0.022 | 42.2 | 379 | 369 | 2.27 | 12.5 | 888 | 0.39 | 108.0 | 2613 | 1611 |
| No. 2 | A | Not recognized | 0.034 | 38.4 | 377 | 372 | 2.30 | 11.3 | 902 | 0.35 | 113.9 | 2650 | 1702 |
| No. 3 | A | Not recognized | 0.053 | 34.1 | 379 | 379 | 2.19 | 11.6 | 943 | 0.30 | 117.6 | 2683 | 1778 |
| No. 4 | A | Not recognized | 0.075 | 38.6 | 390 | 394 | 2.08 | 10.3 | 980 | 0.33 | 119.6 | 2708 | 1832 |
| No. 5 | A | Not recognized | 0.089 | 35.8 | 410 | 414 | 1.97 | 9.7 | 991 | 0.27 | 116.1 | 2727 | 1853 |
| No. 6 | A | Not recognized | 0.105 | 41.8 | 424 | 421 | 1.99 | 10.3 | 1014 | 0.24 | 116.1 | 2625 | 1890 |
| No. 7 | A | Not recognized | 0.122 | 45.7 | 440 | 435 | 1.85 | 9.6 | 1013 | 0.24 | 113.5 | 2323 | 1910 |
| No. 8 | A | Not recognized | 0.138 | 49.9 | 445 | 454 | — | — | — | — | — | 2022 | Not reached |
| No. 9 | B | Not recognized | 0.078 | 0.0 | 431 | 428 | 1.98 | 10.1 | 1011 | 0.20 | 111.7 | 2296 | 1928 |
| Comparative sample No. 1 | A | Not recognized | 0.008 | 46.2 | 358 | 364 | 2.38 | 12.6 | 865 | 0.21 | 93.3 | 2640 | 1575 |
| Comparative sample No. 2 | B | Not recognized | 0.007 | 0.1 | 385 | 387 | 2.20 | 11.2 | 845 | 0.22 | 83.8 | 1948 | 1577 |

3. Results
(1) Structure

FIG. 4 shows examples of photographs of structures of the samples. The Samples Nos. 1 to 8 were subjected to the extruding and had a fine deformed structure composed of an α-β phase as typified by the photograph No. 1 (Sample No. 4) in FIG. 4. The comparative sample No. 1 was also subjected to the extruding and also had a fine deformed structure composed of an α-β phase as shown by the photograph No. 2 (Comparative sample No. 1) in FIG. 4. The fine deformed structure is work hardened due to strain accumulation and contains a great number of grain boundaries that are perpendicular or curved with respect to directions of crack growth, thereby having a great effect for preventing crack growth by stopping and curving cracks. On the other hand, a general type of expanded material of an α-β type titanium alloy has low workability and is normally finished by hot working, thereby having an equiaxed structure. Accordingly, the fine deformed structure is considered to be superior in fatigue resistance to a general type of expanded material of an α-β type titanium alloy having an equiaxed structure that is sold on the market.

In the Samples Nos. 1 to 8 subjected to the hot plastic forming, no pores were observed in the fine deformed structure, which indicates that few pores remaining after the sintering were removed by the extruding and were decreased to zero or almost zero. When there are no pores or pores have small dimensions such as not more than 10 μm even though pores exist, the fatigue resistance is effectively improved because the pores can be origins of fractures. Thus, it is important to perform the hot plastic forming so as to close all pores. In this regard, specifically, the porosity is preferably less than 0.65 pores/mm$^2$ in the fine deformed structure.

The Sample No. 9 and the comparative sample No. 2, which were not hot plastic formed and were subjected to only the heat treatment, had a fine acicular structure as shown by the photograph No. 3 (Sample No. 9) and the photograph No. 4 (Comparative sample No. 2) in FIG. 4. The Sample No. 9 had a greater hardness than the Sample No. 4 that was subjected to only the hot plastic forming and contained the same amount of nitrogen. Similarly, the comparative sample No. 2 had a greater hardness than the comparative sample No. 1. Thus, the hardness can be improved by making the structure of the member so as to have the fine acicular structure by the heat treatment.

(2) TiN Compound Phase

According to the results of the X-ray diffraction, the peaks of nitrogen compounds such as the TiN compound phase were not detected in all of the samples, which indicates that the contained nitrogen did not form nitrogen compounds and were solid solved in the matrix. Existence of nitrogen compounds having a great difference in hardness (or elastic strain) from the matrix is undesirable because the boundary between the nitrogen compound phase and the matrix tends to be origins of fractures and can thereby cause decrease in the fatigue strength. Therefore, the titanium alloy member of the present invention is suitable with respect to fatigue in which repeated stress is loaded, because there is no boundary between a nitrogen compound phase and the matrix, which makes a great difference in the hardness and tends to be an origin of fractures.

(3) Amount of Nitrogen

Figure 5:
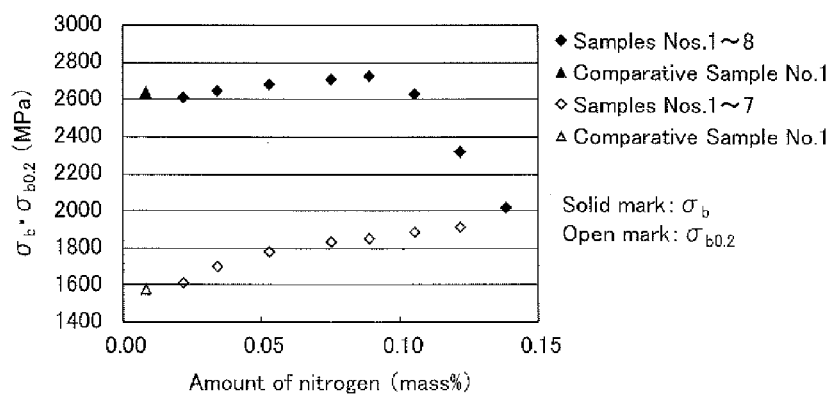
FIG. 5 shows a graph showing a relationship between amount of nitrogen and bending strength or 0.2% bending proof stress of titanium alloy members in the Example.

FIG. 5 is a graph showing a relationship of the amount of nitrogen and bending strength or 0.2% bending proof stress. The Sample No. 1 containing 0.022% of nitrogen had slightly less bending strength than the comparative sample No. 1. However, the Sample No. 1 had greater 0.2% bending proof stress than the comparative sample No. 1 and is suitable for a part to be used under conditions which cause fatigue, because it can be used under higher stresses. As the amount of nitrogen increased, the bending strength and the 0.2% bending proof stress increased until the amount of nitrogen was 0.089% as in the Sample No. 5. Then, in the Sample No. 6 containing 0.105% of nitrogen, the 0.2% bending proof stress further increased, but the ductility decreased, whereby the bending strength decreased to the level of the comparative sample No. 1. This tendency observed when the amount of nitrogen was 0.105% or more increased with the increase in the amount of nitrogen, and the Sample No. 8 containing 0.138% of nitrogen broke before reaching the 0.2% bending proof stress. When the amount of nitrogen was less than 0.02%, the strength and the proof stress were not effectively improved compared with those of the comparative sample No. 1. Accordingly, the titanium alloy member of the present invention preferably contains 0.02 to 0.13% of nitrogen in solid solution.

(4) Area Ratio of Grains with not Less than 3° of Average Misorientation in Grain As shown by the results of the Samples Nos. 1 to 8 subjected to the extruding, the values of "$GOS_{\geq 3°}$" as a parameter for the amount of strain accumulation were much greater than those of the Sample No. 9 and the comparative sample No. 2, which had a fine acicular structure. The fine deformed structure is work hardened due to strain accumulation and contains a great number of grain boundaries that are perpendicular or curved with respect to directions of crack growth, thereby having a great effect for preventing crack growth by stopping and curving cracks, whereby the fatigue resistance can be improved.

(5) Hardness

Figure 6:
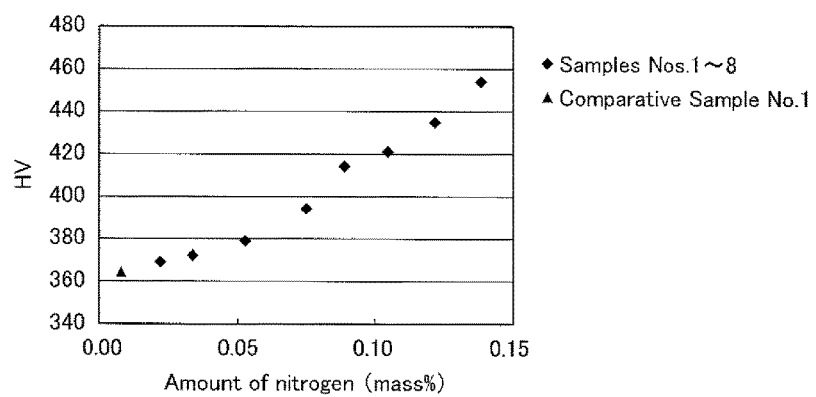
FIG. 6 shows a graph showing a relationship between amount of nitrogen and hardness of titanium alloy members in the Example.

As shown in Table 2, in all of the Samples Nos. 1 to 9, the hardness of the surface and the hardness of the center were approximately the same. The Samples Nos. 1 to 8 had hardness that is equal to or greater than the hardness of the comparative sample No. 1 subjected to the extruding in the same manner. The Sample No. 9 had greater hardness than the comparative sample No. 2 subjected to the heat treatment in the same manner. As shown in FIG. 6, there was a close relationship between the amount of nitrogen and the hardness, and the hardness improved in accordance with the increase in the amount of nitrogen. Thus, according to the present invention, the titanium alloy member can be greatly strengthened in the entirety at the interior portion, and a necessary degree of strength can be obtained.

(6) Surface Roughness

As shown in Table 2, in all of the Samples Nos. 1 to 7, the surface roughness Ra was 2.3 μm or less and the surface roughness Rz was 13 μm or less, which were less than those of the comparative sample No. 1. The Sample No. 9 also had lower surface roughnesses than the comparative sample No. 2. This was because the Samples Nos. 1 to 7 and 9 had high hardness and the surface roughness formed by the shot peening was thereby less than that of the comparative samples Nos. 1 and 2. Thus, the titanium alloy member of the present invention has low roughness that will readily be origins of fractures and thereby has superior fatigue resistance with respect to repeated stress.

(7) 0.2% Bending Proof Stress

Figure 7:
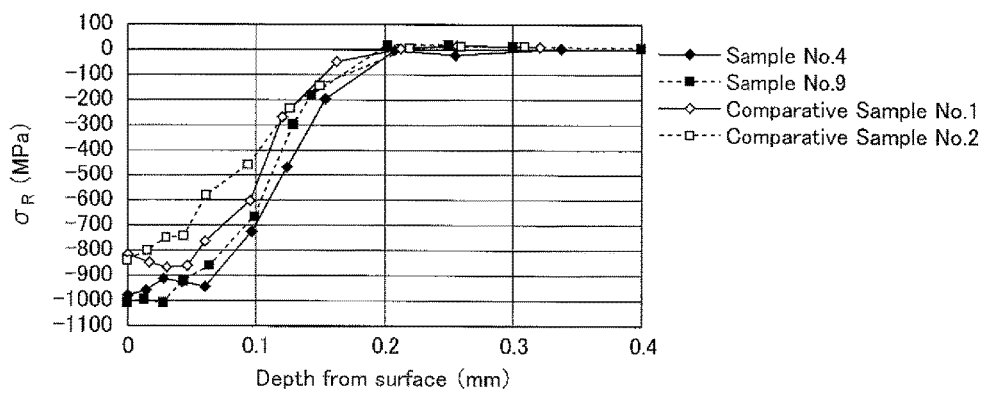
FIG. 7 shows a graph showing a relationship between a depth from a surface and residual stress of titanium alloy members in the Example.

As can be seen in Table 2, the Samples Nos. 1 to 7 and 9 had a high value such that the 0.2% bending proof stress was 1600 MPa or greater. The Samples Nos. 1 to 7 having high proof stress had a maximum compressive residual stress value of 880 MPa or greater and an integrated value of compressive residual stress of 100 MPa·mm or greater, which were greater than those of the comparative sample No. 1. The Samples Nos. 1 to 7 had a crossing point of 0.20 mm or greater and was provided with compressive residual stress from the surface to sufficiently deep in the interior. The Sample No. 9 also had greater compressive residual stress than the comparative sample No. 2 and was provided with compressive residual stress from the surface to sufficiently deep in the interior. FIG. 7 shows compressive residual stress distributions of the Samples Nos. 4 and 9 and the comparative samples Nos. 1 and 2 as examples. As shown in FIG. 7, the Samples Nos. 4 and 9 had a greater compressive residual stress from the surface to deep in the interior compared with the comparative samples Nos. 1 and 2, respectively, and were superior in the fatigue resistance. Such great compressive residual stress from the surface to deep in the interior is obtained proportional to the degree of the proof stress. Thus, by providing high proof stress (yield stress) so that the 0.2% bending proof stress will be 1600 MPa or greater, such great compressive residual stress can be obtained from the surface to the deep interior.

(8) Heat Treatment

In the Sample No. 9, which was not hot plastic formed and was subjected to only the heat treatment, since nitrogen was solid solved at high concentration, the bending strength and the 0.2% bending proof stress were high. The heat treatment solves strain that is accumulated until the heating step. Thus, compressive residual stress was efficiently provided in the surface treating step, and the proof stress was high, whereby high compressive residual stress was obtained. Accordingly, a titanium alloy member having superior fatigue resistance can be obtained only by performing the heat treatment without performing the hot plastic forming.

An average amount of bending deflection of the Sample No. 4 was 3.4 mm whereas that of the Sample No. 9 was 1.9 mm. That is, the Sample No. 9 had greater hardness but slightly less ductility and less toughness compared with the Sample No. 4, which had approximately the same amount of nitrogen and was subjected to the hot plastic forming. Thus, the member subjected to the hot plastic forming had high ductility and high toughness, although the hardness was somewhat low, and is thereby more suitable than the member subjected to the heat treatment when high fatigue resistance is necessary. On the other hand, the member subjected to the heat treatment had high hardness, although the ductility and the toughness were somewhat low, and is thereby suitable when high wear resistance or high fatigue wear resistance is necessary. In some cases, a titanium alloy member may also be produced by performing both the hot plastic forming and the heat treatment. In this case, a member has a fine acicular structure in a condition in which no pores or almost no pores exist, whereby a titanium alloy member which is very superior in fatigue resistance, wear resistance, and fatigue wear resistance is obtained.

The titanium alloy member of the present invention contains 0.02 to 0.13% of nitrogen in solid solution in the entire interior portion and has high strength at the inside and great compressive residual stress from the surface to deep in the interior, thereby being suitably used in parts in which low weight is required and fatigue may be caused by repeated stresses being applied. In particular, the titanium alloy member of the present invention is provided with great compressive residual stress from the surface to deep in the interior, thereby being more suitably used for members that will be repeatedly subjected to bending stress and/or torsional stress, that is, members in which the surface is repeatedly subjected to maximum stress.

The conditions in the sintering and the extruding are not limited to the conditions described in this Example and can be appropriately set in view of obtaining high strength and high proof stress. That is, the densified amount and the degree of diffusion of nitrogen in the sintering and the amount of strain introduced in the plastic forming greatly depend on complicated relationships such as the material composition, the temperature, and the processing rate, and can be determined by appropriately setting conditions based on theory, experience, and experiment.

The conditions for the shot peening are also not limited to the conditions described in this Example, and the conditions such as a suitable apparatus, shot, and injecting speed, are determined in consideration of applied stress and its distribution and the effects on the surface roughness, to provide great compressive residual stress from the surface to deep in the interior.

INDUSTRIAL APPLICABILITY

The titanium alloy material of the present invention is applicable for materials used for aircraft and automobiles required to be light in weight and have high strength, and materials for biological implant devices.

The invention claimed is:

1. A titanium alloy member consisting of a fine deformed structure and containing 0.02 to 0.13 mass % of nitrogen in solid solution, and having a surface provided with compressive residual stress, wherein GOS $_{\geq 3°}$ of the titanium alloy member is 30% or more, when an average misorientation among all pixels in each grain by FE-SEM/EBSD (Electron Back Scatter Diffraction) method is represented by GOS (Grain Orientation Spread) and an area ratio of grains with not less than 3° of the GOS to the entire observation visual field is represented by the GOS $_{\geq 3°}$.

2. The titanium alloy member according to claim 1, wherein the compressive residual stress is 880 MPa or higher at the maximum.

3. The titanium alloy member according to claim 1, wherein the titanium alloy member has an integrated value $I_{-\sigma R}$ of compressive residual stress of 100 MPa·mm or higher, in which the integrated value $I_{-\sigma R}$ is obtained by integrating compressive residual stress from the surface to a crossing point that is a depth from the surface, where the compressive residual stress is zero.

4. The titanium alloy member according to claim 1, wherein the titanium alloy member is made from an α-β type titanium alloy.

5. The titanium alloy member according to claim 1, wherein the titanium alloy member is produced by the following method:
　preparing a raw material made of titanium alloy;
　nitriding the raw material to form a nitrogen-containing raw material by generating a nitrogen compound layer and/or a nitrogen solid solution layer in a surface layer of the raw material;
　mixing the raw material and the nitrogen-containing raw material to yield a nitrogen-containing mixed material;
　sintering the nitrogen-containing mixed material to obtain a sintered titanium alloy member by bonding the material together and uniformly diffusing nitrogen in solid solution from the nitrogen-containing raw material to the entire interior portion of the sintered titanium alloy member;
　hot plastic forming and/or heat treating the sintered titanium alloy member to obtain a processed member; and surface treating the processed member to provide compressive residual stress.

6. A biological implant device produced from the titanium alloy member of claim 1.

7. The titanium alloy member according to claim 1, wherein the titanium alloy member has bending strength of 2650 MPa or higher.

8. The titanium alloy member according to claim 1, wherein the fine deformed structure includes curved grain boundaries.

9. The titanium alloy member according to claim 1, wherein the titanium alloy member is composed of a sintered material.

10. The titanium alloy member according to claim 1, wherein the titanium alloy member has a 0.2% bending proof stress of 1702 MPa or higher and a bending strength of 2296 MPa or higher.

11. A method for producing a titanium alloy member of claim 1, comprising:
preparing a raw material made of titanium alloy;
nitriding the raw material to form a nitrogen-containing raw material by generating a nitrogen compound layer and/or a nitrogen solid solution layer in a surface layer of the raw material;
mixing the raw material and the nitrogen-containing raw material to yield a nitrogen-containing mixed material;
sintering the nitrogen-containing mixed material to obtain a sintered titanium alloy member by bonding the material together and uniformly diffusing nitrogen in solid solution from the nitrogen-containing raw material to the entire interior portion of the sintered titanium alloy member;
hot plastic forming and/or heat treating the sintered titanium alloy member to obtain a processed member; and
surface treating the processed member to provide compressive residual stress.

12. The method for producing the titanium alloy member according to claim 11, wherein the titanium alloy member has a maximum compressive residual stress value of 880 MPa or higher.

13. The method for producing the titanium alloy member according to claim 11, wherein the titanium alloy member has an integrated value $I_{-oR}$ of compressive residual stress of 100 MPa·mm or higher, in which the integrated value $I_{-oR}$ is obtained by integrating compressive residual stress from the surface of the titanium alloy member to a crossing point that is a depth from the surface, where the compressive residual stress is zero.

14. The method for producing the titanium alloy member according to claim 11, wherein the titanium alloy member has 0.2% bending proof stress of 1600 MPa or higher.

15. The method for producing the titanium alloy member according to claim 11, wherein the raw material is made of an α-β type titanium alloy.

16. The method for producing the titanium alloy member according to claim 11, wherein the raw material is a titanium alloy fiber produced by a molten metal extraction method.

17. The method for producing the titanium alloy member according to claim 11, wherein the surface treating is performed by shot peening.

18. The method for producing the titanium alloy member according to claim 11, wherein the sintering is performed by one of hot pressing, hot isostatic pressing, and spark plasma pressure sintering.

* * * * *